United States Patent
Peri et al.

(10) Patent No.: US 8,221,657 B2
(45) Date of Patent: Jul. 17, 2012

(54) NEAR INFRARED ABSORBING PHTHALOCYANINES AND THEIR USE

(75) Inventors: Francesca Peri, Bologna (IT); Cesare Lorenzetti, Grottammare (AP) (IT); Samanta Cimitan, Ponte di Piave (IT); Markus Grob, Reinach (CH)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/152,321

(22) Filed: Jun. 3, 2011

(65) Prior Publication Data

US 2011/0236642 A1 Sep. 29, 2011

Related U.S. Application Data

(63) Continuation of application No. 12/520,896, filed as application No. PCT/EP2007/064465 on Dec. 21, 2007, now abandoned.

(30) Foreign Application Priority Data

Jan. 11, 2007 (EP) .................................... 07100364

(51) Int. Cl.
| | |
|---|---|
| *F21V 9/00* | (2006.01) |
| *G02B 5/02* | (2006.01) |
| *G02C 7/10* | (2006.01) |
| *G02F 1/361* | (2006.01) |
| *G03B 11/00* | (2006.01) |
| *B32B 27/32* | (2006.01) |
| *F21V 9/04* | (2006.01) |
| *F21V 9/06* | (2006.01) |
| *G02B 5/22* | (2006.01) |
| *G02B 5/26* | (2006.01) |

(52) U.S. Cl. ......... 252/582; 252/584; 252/585; 252/587; 252/589; 264/464; 264/478; 428/182; 428/220; 428/339; 428/383; 430/944; 524/88; 540/135; 540/139; 540/140; 977/742; 977/773

(58) Field of Classification Search .................. 252/582, 252/584, 585, 587, 589; 264/464, 478; 428/182, 428/220, 339, 383; 430/944; 524/88; 540/135, 540/139, 140; 977/742, 773
See application file for complete search history.

(56) References Cited

U.S. PATENT DOCUMENTS

| | | |
|---|---|---|
| 5,024,926 A | 6/1991 | Itoh et al. |
| 7,074,351 B2 | 7/2006 | Dobler et al. |
| 2002/0048635 A1 | 4/2002 | Kim et al. |
| 2003/0122114 A1 | 7/2003 | Dobler et al. |

FOREIGN PATENT DOCUMENTS

| | | |
|---|---|---|
| EP | 0337209 A2 | 12/1992 |
| EP | 0519423 | 12/1992 |
| WO | 2006/121174 A1 | 11/2006 |

*Primary Examiner* — Bijan Ahvazi
(74) *Attorney, Agent, or Firm* — Tyler A. Stevenson

(57) ABSTRACT

The instant invention relates to novel phthalocyanines and their use as IR-absorbers, in particular in transparent thermoplastic or crosslinkable polymers. A further aspect of the invention is a composition of these phthalocyanines and thermoplastic or crosslinkable polymers and an architectural or automotive glazing containing these phthatolcyanines.

6 Claims, 1 Drawing Sheet

Evaluation Equipment Layout
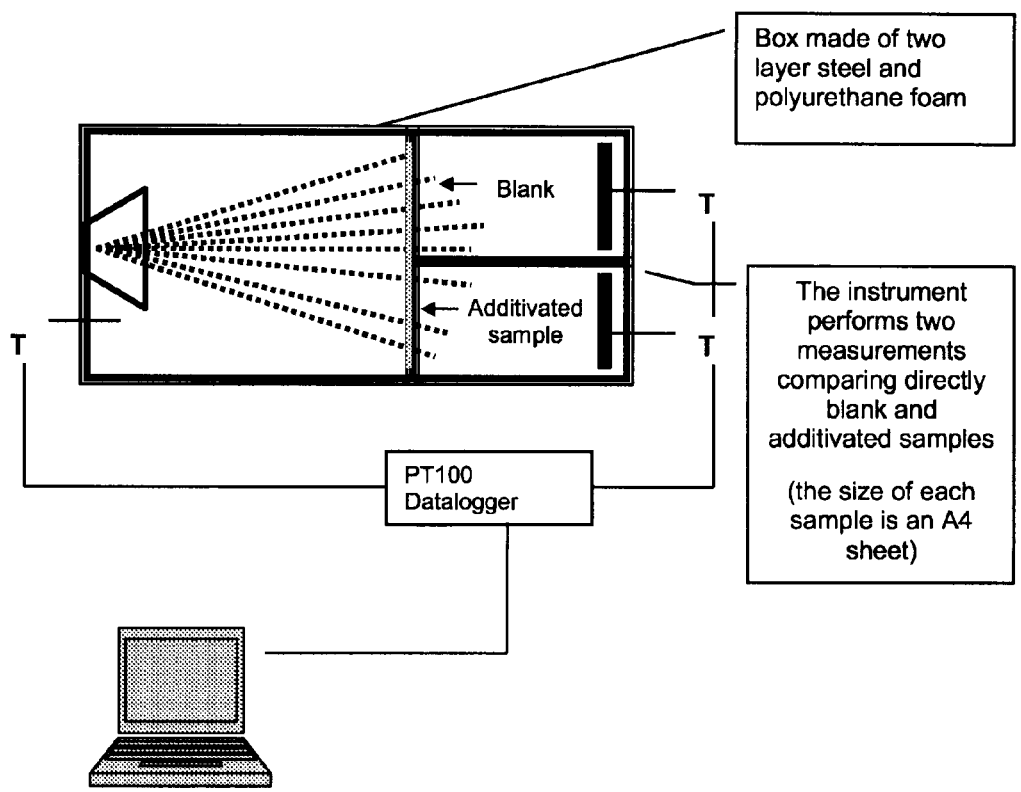

NEAR INFRARED ABSORBING PHTHALOCYANINES AND THEIR USE

This application is a continuation of U.S. application Ser. No. 12/520,896, abandoned, which is a national stage of PCT/EP 2007/064465, filed Dec. 21, 2007, the contents of which applications are incorporated by reference.

The instant invention relates to novel phthalocyanines and their use as IR-absorbers, in particular in transparent thermoplastic or crosslinkable polymers. A further aspect of the invention is a composition of these phthalocyanines and thermoplastic or crosslinkable polymers and an architectural or automotive glazing containing these phthatolcyanines.

The absorption of near infrared radiation (NIR) is an important technical issue in various fields. A significant reduction of the heat transfer into buildings and cars is possible by blocking or filtering the near infrared part of the solar spectrum. This allows a considerable energy saving, mainly due to a smaller demand for air conditioning.

Up to now several solutions have been proposed and more and more have been applied on glazing surfaces of many buildings, such as interference reflective films, semi-conducting or conducting films: they are all able to reflect, with good selectivity, NIR radiation. The so-called "low-e" windows are for example reflective coated mineral or polymeric glasses.

However the production of such coatings is an extremely time consuming step, specially considering that almost all solutions need several layers, and that the durability may be also quite limited due to a generally low scratch resistance. This is, for example, described in WO 2005/072947.

Another approach is the use of bulk additives that absorb the NIR radiation. This approach is less expensive, not time consuming, long lasting and particularly needed for thermoplastic polymers used in glazing. Some examples for polymers used in glazing applications are polycarbonates (PC), polyesters like PET-G, polymethylmethacrylate (PMMA), polyvinylbutyral (PVB) and others. Mainly used for agricultural applications are polyolefin films.

For this purpose several NIR absorbing dyes and pigments have been proposed and are commercially available, such as phthalocyanines and quaterrylenes (i.e.: LUMOGEN® 788 or 765 from BASF).

However these NIR-absorbers do not fully satisfy all technological and market requirements.

It is therefore the object of the instant invention to provide new phthalocyanines, which overcome the deficiencies of the prior art NIR-absorbers.

The present invention provides NIR absorbing phthalocyanines with strong absorption in the NIR region whilest showing low or very low absorption in the visible region Furthermore they combine a high compatibility with a high thermal stability and weather resistance in the most common plastic matrices.

One aspect of the invention is a compound of formula (Ia)

(Ia)

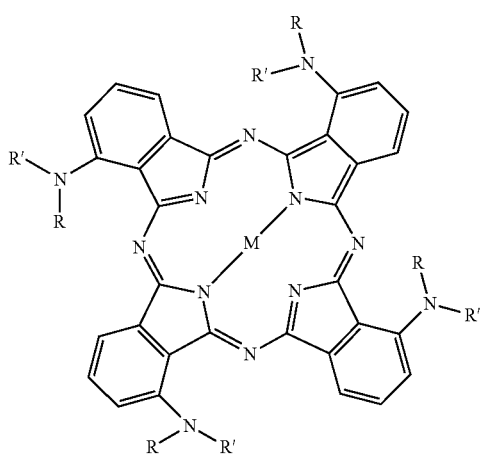

wherein

R is hydrogen, $C_1$-$C_{18}$alkyl, $C_3$-$C_{18}$alkyl interrupted by one or more O atoms, benzyl, cyclohexyl or R and R' together with the nitrogen atom to which they are bonded form a morpholine group;

R' is hydrogen or $C_1$-$C_{18}$alkyl;

M is Mn, Zn, V(O), Ti(O), Si, Al, Sn, Cu and Co with the proviso that if R is methyl and R' is hydrogen, M is not Zn if R and R' are butyl or octyl M is not Sn and if R and R' are methyl M is not Zn, Ti(O), V(O), Cu and Co.

The alkyl radicals may be linear or branched. Examples of alkyl containing 1 to 18 carbon atoms are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, hexadecyl and octadecyl.

$C_3$-$C_{18}$alkyl interrupted by O are for example derived from ethylene glycol or propylene glycol. For example M is Mn, Cu, V(O), Co or Al.

For instance R is $C_1$-$C_{18}$alkyl; R' is H and M is Mn, Cu, V(O), Co or Al.

In a specific embodiment of the invention R is $CH_3$, R' is hydrogen and M is Mn, V(O), Cu or Co.

The preparation of the instant phthalocyanines is carried out in analogy to known synthetic routes.

One possibility is, for example,

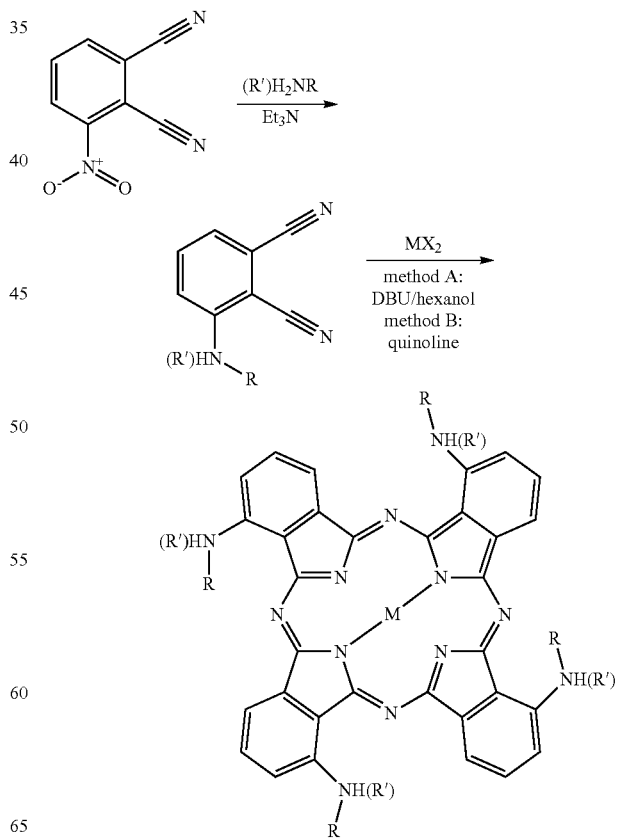

For some metals a second strategy is more useful:

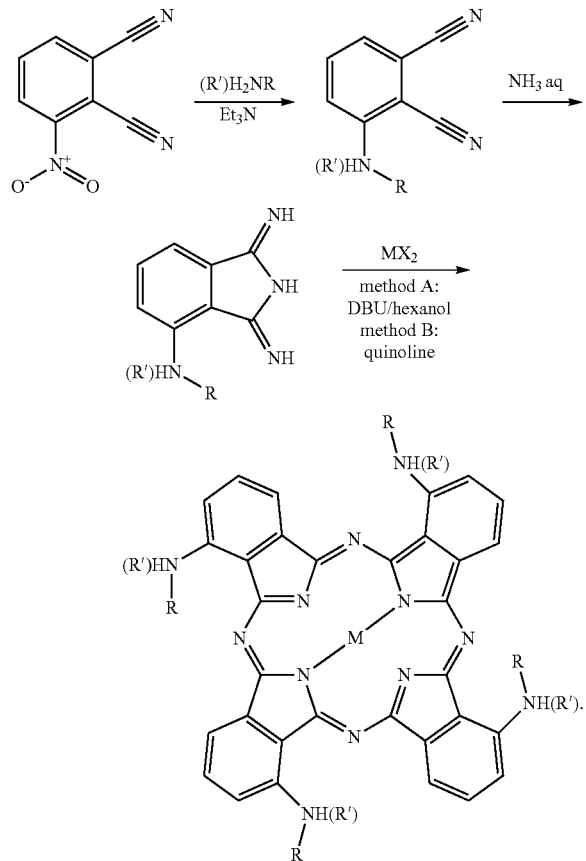

The compounds of formula (Ia) are ideally suitable as IR-absorbers. The great advantage is that these phthalocyanines lead to plastic articles which are highly transparent and essentially colorless.

Consequently another aspect of the invention is a transparent or translucent composition comprising a) a compound of formula (I)

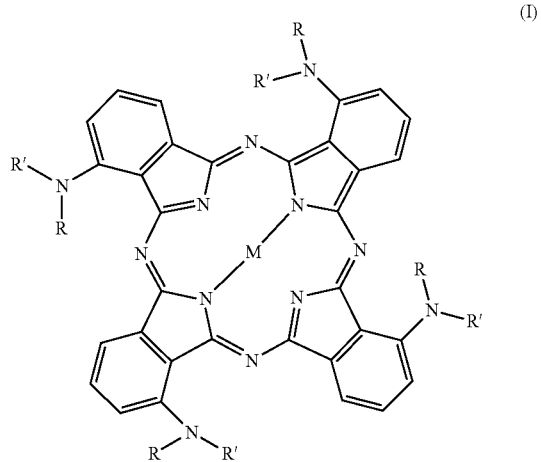

(I)

wherein
R is hydrogen, $C_1$-$C_{18}$alkyl, $C_3$-$C_{18}$alkyl interrupted by one or more O atoms, benzyl, cyclohexyl or R and R' together with the nitrogen atom to which they are bonded form a morpholine group;
R' is hydrogen or $C_1$-$C_{18}$alkyl;
M is Mn, Zn, V(O), Ti(O), Si, Al, Sn, Cu and Co.
which is dispersed in
b) a thermoplastic or crosslinkable polymer.

The amount of light transmitted through the present materials, i.e. degree of translucency or transparency, mainly depends on well known parameters such as the particle loading, further additives used, haze level of the polymer matrix and thickness of the material. The present materials usually are at least 80%, or rather more than 90% translucent in each part of the visible range (400-800 nm); preferred materials have good transparency, and especially are selected from clear-transparent sheets and films of thickness less than 10 mm (e.g. 0.01 to 5 mm). Preferred materials further share one or more of the following advantageous properties:
a full solar radiation transmittance (340-1800 nm) of less than 60%,
a haze of less than 1%, and
a full visible light transmittance (400-800 nm) of more than 75%.

A wide variety of polymers may be used. Examples are given below.
Polycarbonate (PC) or a coating or coextruded layer on polycarbonate, polyesters, acrylics, halogenated polymers such as polyvinylchloride (PVC), polyolefins, aromatic homopolymers and copolymers derived from vinyl aromatic monomers and graft copolymers thereof such as acrylnitril-butadiene-styrene terpolymer (ABS), containing these polymers as major component or in essentially pure form (e.g. 50-100% b.w.), especially:
a polymer selected from PC, polymethylmethacrylate (PMMA), polyethyleneterephthalate (PET, PET-G), PVC, transparent ABS, polyvinylidene fluoride (PVDF), styrene-acrylnitril copolymer (SAN), polypropylene (PP), polyethylene (PE)
including blends, alloys, co-polymers.

Also suitable are polyvinylacetales such as polyvinylbutyral (PVB).

Polymers useful within the present invention include the following ones:
1. Polymers of monoolefins and diolefins, for example polypropylene, polyisobutylene, polybut-1-ene, poly-4-methylpent-1-ene, polyvinylcyclohexane, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:
radical polymerisation (normally under high pressure and at elevated temperature).
  b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is generated in-situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Aromatic homopolymers and copolymers derived from vinyl aromatic monomers including styrene, α-methylstyrene, all isomers of vinyl toluene, especially p-vinyltoluene, all isomers of ethyl styrene, propyl styrene, vinyl biphenyl, vinyl naphthalene, and vinyl anthracene, and mixtures thereof. Homopolymers and copolymers may have any stereostructure including syndiotactic, isotactic, hemi-isotactic or atactic; where atactic polymers are preferred. Stereoblock polymers are also included.

5. Copolymers including aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof, for example styrene/butadiene, styrene/acrylonitrile (SAN), styrene/ethylene (interpolymers), styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

6. Graft copolymers of vinyl aromatic monomers such as styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 4), for example the copolymer mixtures known as ABS, MBS, ASA or AES polymers.

7. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride (PVC), polyvinylidene chloride, polyvinyl fluoride, polyvinylidene fluoride (PVDF), as well as copolymers thereof such as vinyl chloride/vinylidene chloride, vinyl chloride/vinyl acetate or vinylidene chloride/vinyl acetate copolymers.

8. Polymers derived from α,β-unsaturated acids and derivatives thereof such as polyacrylates and polymethacrylates; polymethyl methacrylates (PMMA), polyacrylamides and polyacrylonitriles, impact-modified with butyl acrylate.

9. Polyesters derived from dicarboxylic acids and diols and/or from hydroxycarboxylic acids or the corresponding lactones, for example polyethylene terephthalate (PET), polybutylene terephthalate (PBT), poly-1,4-dimethylolcyclohexane terephthalate, polyalkylene naphthalate (PAN) and polyhydroxybenzoates, as well as block copolyether esters derived from hydroxyl-terminated polyethers; and also polyesters modified with polycarbonates or MBS.

10. Polycarbonates and polyester carbonates, examples have been already given above.

Suitable polyvinylacetales include polymers derived from unsaturated alcohols and amines (i.e. acyl derivatives or acetals thereof), for example polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

Incorporation of the compounds of formula (I) into the polymer matrix leads to plastic articles which are highly transparent; they may be colorless (e.g. for clear glazings or films) or colored, e.g. by addition of a pigment or mixture of pigments, e.g. for applications wherein suitable light filtering or sun screening is desired. The present compounds of formula (I) allow high loading, giving access to high heat shielding effects.

Preferable loadings are from 0.01 to 10%, especially 0.1 to 5% by weight of the final polymer composition.

The above polymers are all thermoplastic polymers. It is however also possible to incorporate the instant phthalocyanines into a curable/crosslinkable coating, which is applied to a transparent substrate, such as glass or one of the polymers mentioned above. Examples for curable/crosslinkable coatings are given below.

1. Crosslinked polymers derived from aldehydes on the one hand and phenols, ureas and melamines on the other hand, such as phenol/formaldehyde resins, urea/formaldehyde resins and melamine/formaldehyde resins.
2. Drying and non-drying alkyd resins.
3. Unsaturated polyester resins derived from copolyesters of saturated and unsaturated dicarboxylic acids with polyhydric alcohols and vinyl compounds as crosslinking agents, and also halogen-containing modifications thereof of low flammability.
4. Crosslinkable acrylic resins derived from substituted acrylates, for example epoxy acrylates, urethane acrylates or polyester acrylates.
5. Alkyd resins, polyester resins and acrylate resins crosslinked with melamine resins, urea resins, isocyanates, isocyanurates, polyisocyanates or epoxy resins.
6. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

In general thermoplastic polymers are preferred.

Preferably the thermoplastic or crosslinkable polymer comprises polycarbonate, a coating or coextruded layer on polycarbonate, polyesters, acrylics, halogenated polymers, such as polyvinylchloride, polyolefins, aromatic homopolymers and copolymers derived from vinyl aromatic monomers and graft copolymers thereof such as acrylnitril-butadiene-styrene terpolymer, and polyvinylacetales; as well as blends, alloys and co-polymers thereof.

In a specific embodiment of the invention the thermoplastic or crosslinkable polymer comprises polycarbonate, polymethylmethacrylate, polyethyleneterephthalate, polyvinylchloride, transparent ABS, polyvinylidene fluoride, styrene-acrylnitril copolymer, polypropylene, polyethylene, or mixtures thereof.

The composition described above may contain as further component a conventional additive selected from processing additives, antioxidants, flame retardants, clarifiers, UV absorbers and/or sterically hindered amines. Examples are given below.

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl)phenol, 2,4-dimethyl-6-(1'-methylheptadec-1'-yl) phenol, 2,4-dimethyl-6-(1'-methyltridec-1'-yl)phenol and mixtures thereof.

1.2. Alkylthiomethylphenols for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxy-phenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis (3,5-di-tert-butyl-4-hydroxyphenyl) adipate.

1.4. Tocopherols, for example α-tocopherol, β-tocopherol, γ-tocopherol, δ-tocopherol and mixtures thereof (vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl)-disulfide.

1.6. Alkylidenebisphenols, for example 2,2'-methylenebis (6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butyl-phenol), 2,2'-ethylidenebis(6-tert-butyl-4-isobutylphenol), 2,2'-methylenebis [6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl) butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis(3,5-di-tert-butyl-4-hydroxyphenyl)propane, 2,2-bis(5-tert-butyl-4-hydroxy2-methylphenyl)-4-n-dodecylmercaptobutane, 1,1,5,5-tetra-(5-tert-butyl-4-hydroxy-2-methylphenyl)pentane.

1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis(3,5-di-tert-butyl-2-hydroxybenzyl)malonate, dioctadecyl-2-(3-tert-butyl-4-hydroxy-5-methylbenzyl)malonate, di-dodecylmercaptoethyl-2,2-bis(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl) malonate.

1.9. Aromatic hydroxybenzyl compounds, for example 1,3,5-tris(3,5-di-tert-butyl-4-hydroxy-benzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxy-anilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4, 6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates for example dimethyl-2,5-di-tert-butyl-4-hydroxybenzylphosphonate, diethyl-3,5-di-tert-butyl-4-hydroxybenzylphosphonate, dioctadecyl-3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane.

1.14. Esters of β-(5-tert-butyl-4-hydroxy-3-methylphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane; 3,9-bis[2-{3-(3-tert-butyl-4-hydroxy-5-methylphenyl)propionyloxy}-1,1-dimethylethyl]-2,4,8,10-tetraoxaspiro[5.5]-undecane.

1.15. Esters of β-(3,5-dicyclohexyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis (hydroxyethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis (hydroxyethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis(3,5-di-tert-butyl-4-hydroxy-phenylpropionyl)trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl] propionyloxy)ethyl]oxamide (Naugard®XL-1, supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis (4-methoxyphenyl)amine, 2,6-di-tert-butyl-4-dimethylamino-methylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino] ethane, 1,2-bis(phenyl-amino)propane, (o-tolyl)biguanide, bis[4-(1,3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octyl-phenothiazines, a mixture of mono- and dialkylated tert-octylphenothiazines, N-allylphenothiazine, N,N,N',N'-tetraphenyl-1,4-diaminobut-2-ene.

2. UV Absorbers and Light Stabilizers 2.1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)benzotriazole, 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl) phenyl)benzotriazole, 2-(3'-tert-butyl-2'-hydroxy-5'-(2-octyloxycarbonyl-ethyl)phenyl)benzotriazole, 2-(3'-tert-butyl-5'-[2-(2-ethylhexyloxy)carbonylethyl]-2'-hydroxyphenyl) benzotriazole, 2-(3'-dodecyl-2'-hydroxy-5'-methylphenyl) benzotriazole, 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300;

where R=3'-tert-butyl-4'-hydroxy-5'-2H-benzotriazol-2-ylphenyl, 2-[2'-hydroxy-3'-(α,α-dimethylbenzyl)-5'-(1,1,3, 3-tetramethylbutyl)-phenyl]-benzotriazole; 2-[2'-hydroxy-3'-(1,1,3,3-tetramethylbutyl)-5'-(α,α-dimethylbenzyl)-phenyl]benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example 4-tert-butyl-phenyl salicylate, phenyl salicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate, N-(β-carbomethoxy-β-cyanovinyl)-2-methylindoline, neopentyl tetra(α-cyano-β,β-diphenylacrylate.

2.5. Nickel compounds for example nickel complexes of 2,2'-thio-bis[4-(1,1,3,3-tetramethyl-butyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenylundecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butanetetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)-malonate, 3-n-octyl-7,7,9,9-tetramethyl-1,3,8-triazaspiro[4.5]decane-2,4-dione, bis(1-octyloxy-2,2,6,6-tetramethylpiperidyl)sebacate, bis(1-octyloxy-2,2,6,6-tetramethylpiperidyl)succinate, linear or cyclic condensates of N,N'-bis(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl) pyrrolidine-2,5-dione, a mixture of 4-hexadecyloxy- and 4-stearyloxy-2,2,6,6-tetramethylpiperidine, a condensate of N,N'-bis(2,2,6,6-tetramethyl-4-piperidyl)hexamethylenediamine and 4-cyclohexylamino-2,6-dichloro-1,3,5-triazine, a condensate of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); a condensate of 1,6-hexanediamine and 2,4,6-trichloro-1,3,5-triazine as well as N,N-dibutylamine and 4-butylamino-2,2,6,6-tetramethylpiperidine (CAS Reg. No. [192268-64-7]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxospiro[4,5]decane, a reaction product of 7,7,9,9-tetramethyl-2-cycloundecyl-1-oxa-3,8-diaza-4-oxospiro-[4,5]decane and epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl)hexamethylenediamine, a diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, a reaction product of maleic acid anhydride-α-olefin copolymer with 2,2,6,6-tetramethyl-4-aminopiperidine or 1,2,2,6,6-pentamethyl-4-aminopiperidine, 2,4-bis[N-(1-cyclohexyloxy-2,2,6,6-tetramethylpiperidine-4-yl)-N-butylamino]-6-(2-hydroxyethyl)amino-1,3,5-triazine, 1-(2-hydroxy-2-methylpropoxy)-4-octadecanoyloxy-2,2,6,6-tetramethylpiperidine, 5-(2-ethylhexanoyl)oxymethyl-3,3,5-trimethyl-2-morpholinone, Sanduvor (Clariant; CAS Reg. No. [106917-31-1], 5-(2-ethylhexanoyl)oxymethyl-3,3,5-trimethyl-2-morpholinone, the reaction product of 2,4-bis[(1-cyclohexyloxy-2,2,6,6-piperidine-4-yl)butylamino]-6-chloro-s-triazine with N,N'-bis(3-aminopropyl) ethylenediamine), 1,3,5-tris(N-cyclohexyl-N-(2,2,6,6-tetramethylpiperazine-3-one-4-yl)amino)-s-triazine, 1,3,5-tris(N-cyclohexyl-N-(1,2,2,6,6-pentamethylpiperazine-3-one-4-yl)-amino)-s-triazine.

2.7. Oxamides, for example 4, 4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy)phenyl]-4,6-bis(2,4-dimethyl)-1,3,5-triazine, 2-[2-hydroxy-4-(2-hydroxy-3-octyloxypropyloxy)phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-hexyloxy) phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine, 2,4-bis(4-[2-ethylhexyloxy]-2-hydroxyphenyl)-6-(4-methoxyphenyl)-1,3,5-triazine.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenylalkyl phosphites, phenyldialkyl phosphites, tris(nonylphenyl) phosphite, trilauryl phosphite, trioctadecyl phosphite, distearylpentaerythritol diphosphite, tris(2,4-di-tert-butylphenyl) phosphite, diisodecyl pentaerythritol diphosphite, bis(2,4-di-tert-butylphenyl)pentaerythritol diphosphite, bis(2,4-di-cumylphenyl)pentaerythritol diphosphite, bis(2,6-di-tert-butyl-4-methylphenyl)pentaerythritol diphosphite, diisodecyloxypentaerythritol diphosphite, bis(2,4-di-tert-butyl-6-methylphenyl)-pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 6-fluoro-2,4,8,10-tetra-tert-butyl-12-methyl-dibenz[d,g]-1,3,2-dioxaphosphocin, 2,2',2''-nitrilo-[triethyltris(3,3',5,5'-tetra-tert-butyl-1,1'-biphenyl-2,2'-diyl) phosphite], 2-ethylhexyl(3,3',5,5'-tetra-tert-butyl-1,1'-biphenyl-2,2'-diyl)phosphite, 5-butyl-5-ethyl-2-(2,4,6-tri-tert-butylphenoxy)-1,3,2-dioxaphosphirane.

The following phosphites are especially preferred:

Tris(2,4-di-tert-butylphenyl) phosphite (Irgafos®168, Ciba Specialty Chemicals Inc.), tris(nonylphenyl) phosphite,

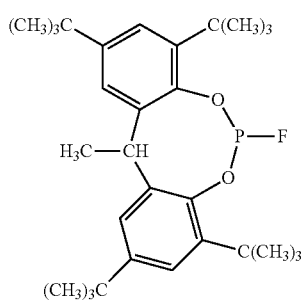

(A)

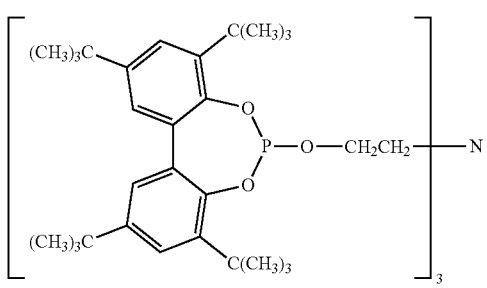

(B)

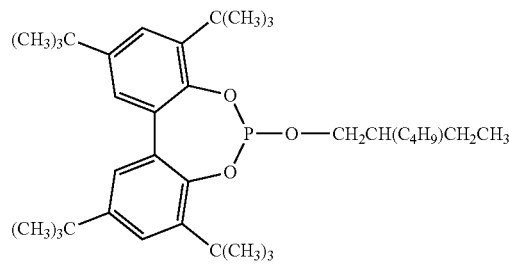

(C)

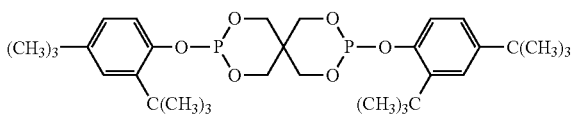

(D)

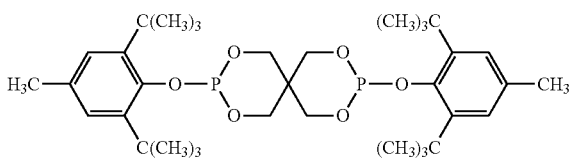

(E)

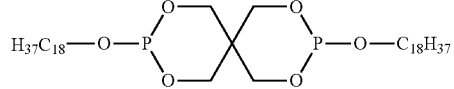

(F)

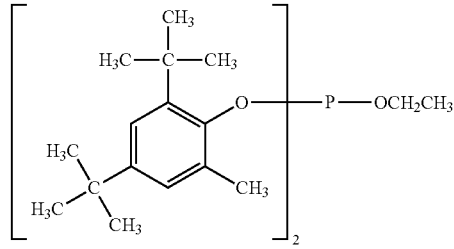

(G)

5. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxy-ylamine, N-heptadecyl-N-octadecylhydroxylamine, N,N-dialkylhydroxylamine derived from hydrogenated tallow amine.

6. Nitrones, for example, N-benzyl-alpha-phenylnitrone, N-ethyl-alpha-methylnitrone, N-octyl-alpha-heptylnitrone, N-lauryl-alpha-undecylnitrone, N-tetradecyl-alpha-tridecylnnitrone, N-hexadecyl-alpha-pentadecylnitrone, N-octadecyl-alpha-heptadecylnitrone, N-hexadecyl-alpha-heptadecylnitrone, N-octadecyl-alpha-pentadecylnitrone, N-heptadecyl-alpha-heptadecylnitrone, N-octadecyl-alpha-hexadecylnitrone, nitrone derived from N,N-dialkylhydroxylamine derived from hydrogenated tallow amine.

7. Thiosynergists, for example dilauryl thiodipropionate, dimistryl thiodipropionate, distearyl thiodipropionate or distearyl disulfide.

8. Peroxide scavengers, for example esters of β-thiodipropionic acid, for example the lauryl, stearyl, myristyl or tridecyl esters, mercaptobenzimidazole or the zinc salt of 2-mercapto-benzimidazole, zinc dibutyldithiocarbamate, dioctadecyl disulfide, pentaerythritol tetrakis(β-dodecylmercapto)propionate.

9. Polyamide stabilizers, for example copper salts in combination with iodides and/or phosphorus compounds and salts of divalent manganese.

10. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate and potassium palmitate, antimony pyrocatecholate or zinc pyrocatecholate.

11. Nucleating agents, for example inorganic substances, such as talcum, metal oxides, such as titanium dioxide or magnesium oxide, phosphates, carbonates or sulfates of, preferably, alkaline earth metals; organic compounds, such as mono- or polycarboxylic acids and the salts thereof, e.g. 4-tert-butylbenzoic acid, adipic acid, diphenylacetic acid, sodium succinate or sodium benzoate; polymeric compounds, such as ionic copolymers (ionomers). Especially preferred are 1,3:2,4-bis(3',4'-dimethylbenzylidene)sorbitol, 1,3:2,4-di(paramethyldibenzylidene)sorbitol, and 1,3:2,4-di(benzylidene)sorbitol.

12. Fillers and reinforcing agents, for example calcium carbonate, silicates, glass fibres, glass beads, asbestos, talc, kaolin, mica, barium sulfate, metal oxides and hydroxides, carbon black, graphite, wood flour and flours or fibers of other natural products, synthetic fibers.

13. Other additives, for example plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. Nos. 4,325,863; 4,338,244; 5,175,312; 5,216,052; 5,252,643; DE-A-4316611; DE-A-4316622; DE-A-4316876; EP-A-0589839, EP-A-0591102; EP-A-1291384 or 3-[4-(2-acetoxyethoxy)phenyl]-5,7-di-tert-butylbenzofuran-2-one, 5,7-di-tert-butyl-3-[4-(2-stearoyloxy-ethoxy)phenyl]benzofuran-2-one, 3,3'-bis[5,7-di-tert-butyl-3-[4-(2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butylbenzofuran-2-one, 3-(3,5-dimethyl-4-pivaloyloxyphenyl)-5,7-di-tert-butylbenzofuran-2-one, 3-(3,4-dimethylphenyl)-5,7-di-tert-butylbenzofuran-2-one, dimethylphenyl)-5,7-di-tert-butylbenzofuran-2-one, 3-(2-acetyl-5-isooctylphenyl)-5-isooctyl-benzofuran-2-one.

Specific UV-absorbers to be mentioned in the present invention are the following:

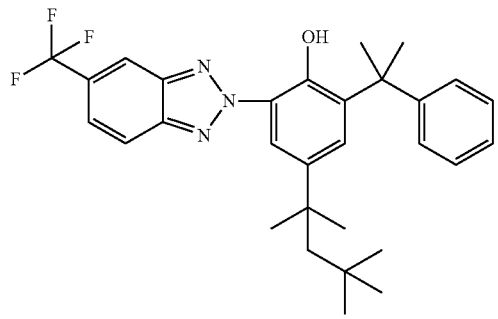

CGL 139

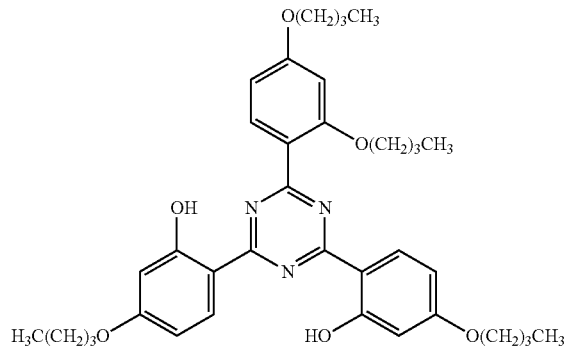

CG 36-1644

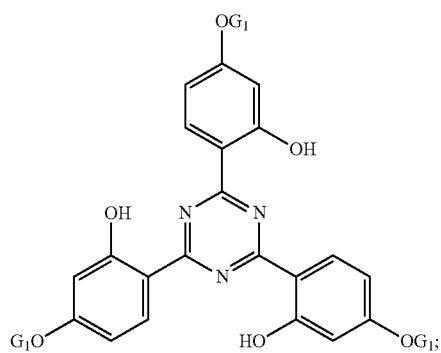

CG 39-0019

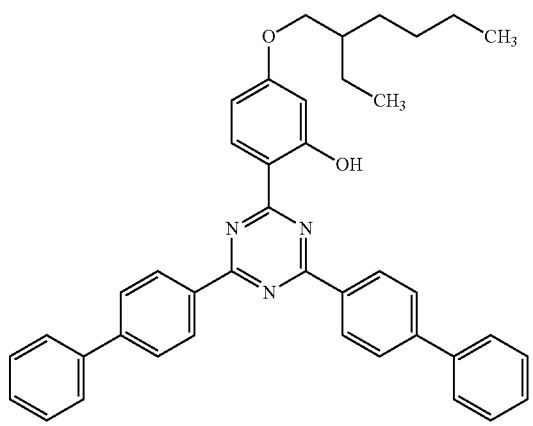

CG 36-1600

-continued
CGL-479
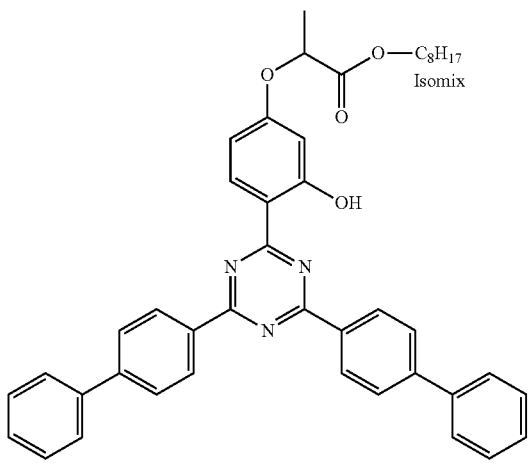
Isomix
CGL-777
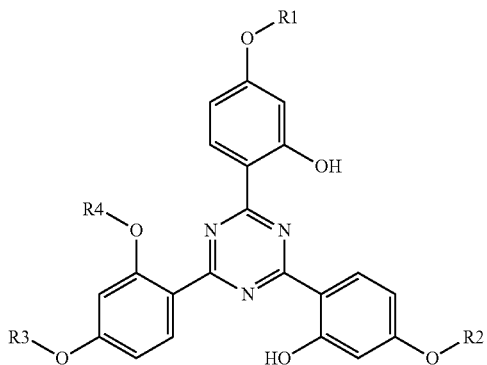
= a mixture of
a) R1 = R2 = CH(CH₃)—COO—C₈H₁₇, R3 = R4 = H;
b) R1 = R2 = R3 = CH(CH₃)—COO—C₈H₁₇, R4 = H;
c) R1 = R2 = R3 = R4 = CH(CH₃)—COO—C₈H₁₇
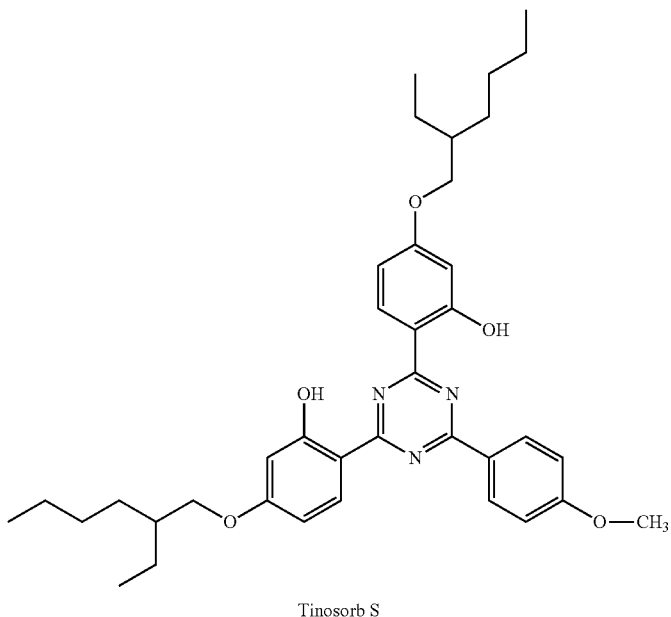
Tinosorb S
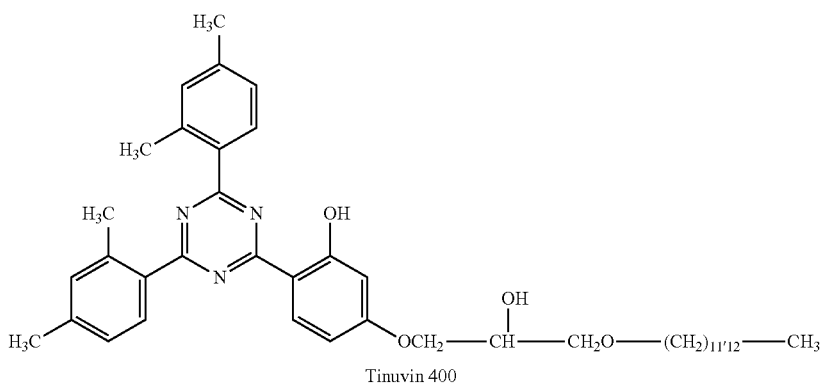
Tinuvin 400

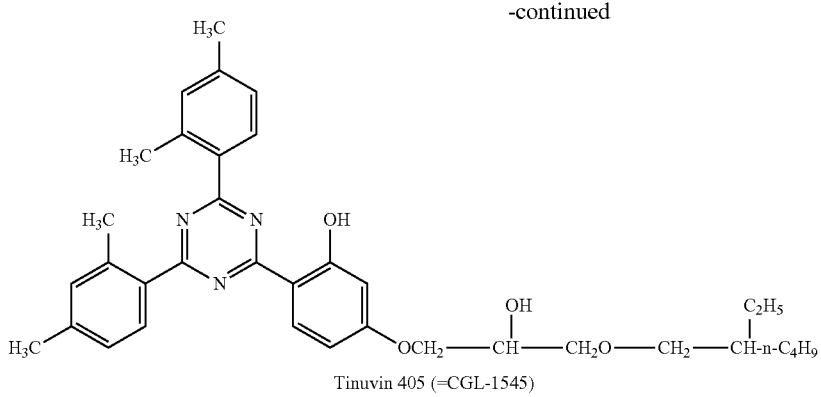
Tinuvin 405 (=CGL-1545)

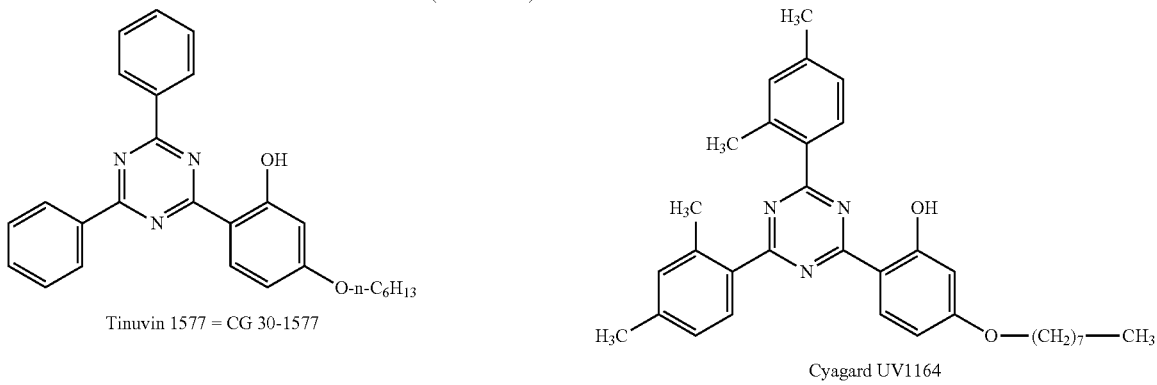
Tinuvin 1577 = CG 30-1577

Cyagard UV1164

T. 776 of Adeka Argus:

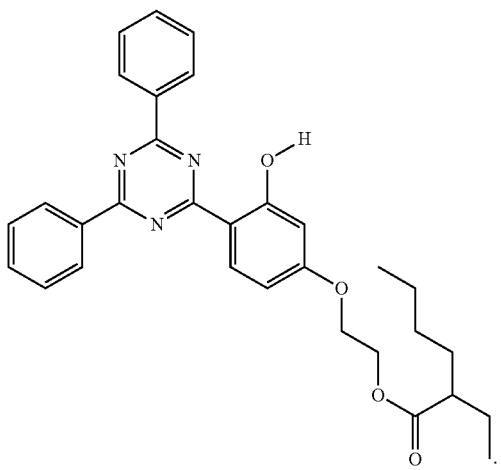

The hydroxyphenyl triazine UV-absorbers are known and are partially items of commerce.

The most suitable benzotriazole UV-absorbers are commercially available under the Trade Names TINUVIN 213®, TINUVIN 326®, TINUVIN 900®, TINUVIN 328® and TINUVIN 350® TINUVIN 360®, TINUVIN 571®.

One or more of these further additives are usually contained in an amount of 0.01 to about 10 of the composition, often in a concentration level of about 0.1 to 5% by weight of the final composition. Important are, for example, antioxidants (e.g. phenolic antioxidants and/or phosph(on)ites listed above) and, for many applications, flame retardants. Clarifiers/nucleating agents may be added to provide or improve transparency, especially in polyolefin compositions. Especially preferred is the combination of the present phthalocyanines with light stabilizers such as UV absorbers and/or sterically hindered amines (HALS).

In another embodiment of the invention further to the phthalocyanines of formula (I) there may be present in the composition as further component solid nano-scaled particles of a thickness of less than 200 nm, which consist of an oxide of zinc and/or a nitride of a transition metal of group III, IV, V, VI of the periodic system, each of which is doped with one or more of the elements belonging to main groups III and IV of the periodic system, or consist of undoped vanadium nitride or scandium nitride.

In particular the nitride is selected from nitrides of scandium, yttrium, lanthanum including the lanthanides, titanium, zirconium, hafnium, vanadium, niobium, tantalum, chromium, molybdenum, wolfram; the doping elements are selected from boron, aluminum, gallium, indium, thallium, carbon, silicon, germanium, tin, lead; the particle preferably consisting of aluminum doped zinc oxide, indium doped zinc oxide, gallium doped zinc oxide, aluminum doped titanium nitride, indium doped titanium nitride, gallium doped titanium nitride, aluminum doped vanadium nitride, indium doped vanadium nitride, gallium doped vanadium nitride, vanadium nitride, aluminum doped scandium nitride, indium doped scandium nitride, gallium doped scandium nitride, scandium nitride.

Useful oxides are, for example, doped zinc oxides such as
AZO (Aluminum Zinc Oxide)
IZO (Indium Zinc Oxide)
GaZO (Gallium Zinc Oxide)

Examples of nitride and doped nitride materials useful as further components in the invention are the following ones:
AlTiN (titanium nitride doped with Aluminium)
InTiN (titanium nitride doped with Indium)
GaTiN (titanium nitride doped with Gallium)
VN (vanadium nitride)
AlVN (vanadium nitride doped with Aluminium)
InVN (vanadium nitride doped with Indium)
GaVN (vanadium nitride doped with Gallium)
ScN (scandium nitride)
AlScN (scandium nitride doped with Aluminium)
InScN (scandium nitride doped with Indium)
GaScN (scandium nitride doped with Gallium)

Normal Zinc Oxide shows no absorption in the NIR region: doping transforms the not conducting in a conducting material which shows absorption in the NIR region.

Regarding the doping level, the present oxides and nitrides may be represented by the formulae:

$$X_a Zn_b O_c \qquad (II)$$

$$X_a Y_d N_e \qquad (III)$$

where X is one or more of the elements belonging to main group III and/or IV of the periodic system, Y is a transition metal belonging to group III, IV, V and/or VI (see above for more details of elements belonging to these groups); indices a-e indicate the abundance of the components, with formula (II) obeying to the condition a<b<c, and formula (III) obeying to the condition a<d less or equal to e. Doping levels, for example of Al, Ga and/or In in ZnO or TiN, often are in the range 0.01 to about 20, especially 0.1 to 10% by weight of the final particle material. The nanoparticles are solid and often, but not necessarily, cristalline. They may be prepared according to methods known in the art, e.g. using sputtering, thermal evaporation, chemical vapor deposition (CVD), spray pyrolysis and sol-gel processes; the materials often are commercially available.

Preferred materials are zinc oxide doped with Al, Ga, In; titanium nitride doped with Al; vanadium nitride or especially scandium nitride; or vanadium nitride or especially scandium nitride doped with Al, Ga, In. Of special importance are Ga or especially Al as doping elements.

Also of special interest are the following materials: ATO (Tin oxide doped with Antimony), ITO (Tin oxide doped with Indium), AZO (Zinc oxide doped with Aluminum), IZO (Zinc oxide doped with Indium), GaZO (Zinc oxide doped with Gallium), $LaB_6$ and doped tungsten oxides ($YWO_x$). Silver or gold nanoparticles, nanoprisms or nanorods, carbon nanotubes.

Such doped oxides and their use in IR shielding applications are for example described in US 2003/0122114 and U.S. Pat. No. 7,074,351.

One or more of these materials may be used.

The nanoparticles of the oxides or nitrides used as further components within the present invention are found not to interact with light as reflectors but as absorbers (scattering is present but gives only a small contribution).

Plastic materials, especially films of the present invention, containing polymers and nanoparticles as described above, advantageously may be used in technical application fields such as architectural glazing, glazing in building and construction, automotive glazing, transportation glazing, agricultural films and structures. The materials may be solid sheets, monolithic sheets, twin-wall sheets, multi-wall sheets, flat sheets, corrugated sheets, films, oriented or mono- or biaxially oriented films, lamination films, capstock films.

Specific application fields include wintergarden and veranda buildings, facades, skylights, pool covers and enclosures, roof structures, vaults, walkways, shelters, signage, interior and exterior design elements, sun shades, side window, rear window, panorama roof, greenhouses.

Main applications are heat-shielding, light management, heat management, energy management, solar control; also of importance are laser welding, security features, marking, tracers, heat transfer.

Compositions of the invention preferably are unplasticized. Compositions of the invention do not require metals or metallic particles and usually do not contain such components. Of special technical interest are rigid, transparent compositions, such as plates or sheets, for automotive or architectural glazings, or translucent or transparent polyolefin or polyolefin copolymer films, especially for agricultural applications.

The additives of the invention and optional further components may be added to the polymer material individually or mixed with one another. If desired, the individual components can be mixed with one another before incorporation into the polymer for example by dry blending, compaction or in the melt.

The incorporation of the additives of the invention and optional further components into the polymer is carried out by known methods such as dry blending in the form of a powder, or wet mixing in the form of solutions, dispersions or suspensions for example in an inert solvent, water or oil. The additives of the invention and optional further additives may be incorporated, for example, before or after molding or also by applying the dissolved or dispersed additive or additive mixture to the polymer material, with or without subsequent evaporation of the solvent or the suspension/dispersion agent. They may be added directly into the processing apparatus (e.g. extruders, internal mixers, etc), e.g. as a dry mixture or powder or as solution or dispersion or suspension or melt.

The incorporation can be carried out in any heatable container equipped with a stirrer, e.g. in a closed apparatus such as a kneader, mixer or stirred vessel. The incorporation is preferably carried out in an extruder or in a kneader. It is immaterial whether processing takes place in an inert atmosphere or in the presence of oxygen.

The addition of the additive or additive blend to the thermoplastic polymer can be carried out in all customary mixing machines in which the polymer is melted and mixed with the additives. Suitable machines are known to those skilled in the art. They are predominantly mixers, kneaders and extruders.

The process is preferably carried out in an extruder by introducing the additive during processing.

Particularly preferred processing machines are single-screw extruders, contrarotating and corotating twin-screw extruders, planetary-gear extruders, ring extruders or cokneaders. It is also possible to use processing machines provided with at least one gas removal compartment to which a vacuum can be applied.

Suitable extruders and kneaders are described, for example, in *Handbuch der Kunststoffextrusion, Vol. 1 Grundlagen*, Editors F. Hensen, W. Knappe, H. Potente, 1989, pp. 3-7, ISBN:3-446-14339-4 (Vol. 2 *Extrusionsanlagen* 1986, ISBN 3-446-14329-7).

For example, the screw length is 1-60 screw diameters, preferably 20-48 screw diameters. The rotational speed of the screw is preferably 1-800 rotations per minute (rpm), very particularly preferably 25-400 rpm.

The maximum throughput is dependent on the screw diameter, the rotational speed and the driving force. The process of the present invention can also be carried out at a level lower than maximum throughput by varying the parameters mentioned or employing weighing machines delivering dosage amounts.

If a plurality of components is added, these can be premixed or added individually.

The additives of the invention and optional further additives can also be added to the polymer in the form of a masterbatch ("concentrate") which contains the components in a concentration of, for example, about 1% to about 40% and preferably 2% to about 20% by weight incorporated in a polymer. The polymer must not be necessarily of identical structure than the polymer where the additives are added finally. In such operations, the polymer can be used in the form of powder, granules, solutions, suspensions or in the form of latices.

Incorporation can take place prior to or during the shaping operation, or by applying the dissolved or dispersed compound to the polymer, with or without subsequent evaporation of the solvent. A further possibility for incorporating the additives of the invention into polymers is to add them before, during or directly after the polymerization of the corresponding monomers or prior to crosslinking. In this context the additive of the invention can be added as it is or else in encapsulated form (for example in waxes, oils or polymers).

The materials containing the additives of the invention described herein can be used for the production of moldings, rotomolded articles, injection molded articles, blow molded articles, films, tapes, mono-filaments, fibers, nonwovens, profiles, adhesives or putties, surface coatings and the like.

A further aspect of the invention is a process for the preparation of a transparent or translucent heat shielding material, which process comprises the addition of a compound of formula (I) as described above to a thermoplastic or crosslinkable polymer.

Yet other aspects of the invention are the use of a compound as described above as a heat shielding additive in a thermoplastic or crosslinkable polymer matrix and the use of the transparent or translucent composition as described above as a heat shielding architectural or automotive glazing or agricultural film.

In another aspect, the invention relates also to the use of compounds of formula (I) for laser welding, paper printing and security printing.

The definitions and preferences given above apply also for the other aspects of the invention.

BRIEF DESCRIPTION OF THE DRAWINGS

FIG. 1 shows the apparatus employed to measure the heat shielding factor after 900 seconds, as expressed by ΔT(° C.)/900 for a 300 micron PET-G film containing present additive compound 101 vs. a film containing none of the present additives. The instrument compares the temperature build up of a black aluminum panel behind two plastic samples (A4 size), one sample containing the solar controlling additive and the other being a reference without any additive. The two samples are mounted on the front side of two different chambers that are exposed to light of a 500 W halogen lamp with a color temperature of 5000 K. Two probes PT100 are connected to a PC data logger. Results are described in Examples B3 and C.

The following examples illustrate the invention.

A) PREPARATION EXAMPLES

Intermediate Compound 1

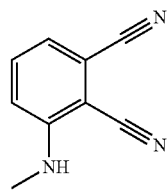

Intermediate compound 1

3-nitro-aminophthalonitrile (100 g), and triethylamine (116.3 g) are dissolved in N,N-dimethylacetamide (200 ml). The mixture is stirred. An aqueous solution of methylamine (40%) is heated and the gaseous solution is bubbled into the reaction mixture at 30-35° C. until the starting material has disappeared. The reaction is followed via thin layer chromatography (TLC), (toluene: THF 1:1). The mixture is then transferred into 600 ml of water and let stirring for 1 h at 25° C. The precipitate is filtered and washed with water. It is then re-dispersed in xylene and heated so that the water is distilled off. Once cooled down, the product precipitates. The crude product is filtered and washed with xylene and n-hexane, then dried under vacuum overnight at 60° C. 74 g of a yellow solid are obtained (yield: 82%).

mp: 177-179° C.

$^1$H NMR (CDCl$_3$, 300 MHz): δ 6.77-7.56 (m, 3H); 5.0 (br s, 1H); 2.9 (d, 3H).

The following intermediate compounds are prepared in analogy to the above example.

| Intermediate compound number | Amine used | Structure obtained | Yield (%) | m.p. (° C.) |
|---|---|---|---|---|
| 2 | NH$_2$Et aq | 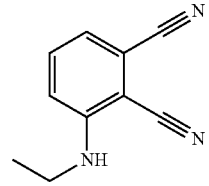 | 67 | 120-122 |

-continued

| Intermediate compound number | Amine used | Structure obtained | Yield (%) | m.p. (° C.) |
|---|---|---|---|---|
| 3 | NH₂—n-Bu | | 93 | 92-94 |
| 4 | NH₂-n-octyl | | 70 | 63-66 |
| 5 | NH₂-Cy | | 34 | 106-108 |
| 6 | Morpholine | | 64 | 168-170 |
| 7 | EtO(CH₂)₃NH₂ | | 71 | 67-70 |
| 8 | PhCH₂NH₂ | | 48 | 159-162 |
| 9 | Me₂NH | 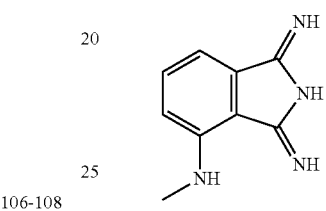 | 84 | 119-121 |

Intermediate Compound 10

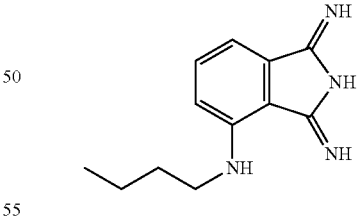

In a 500 ml reaction flask, 130 g of the intermediate compound 1 (0.47 mol) are dissolved in THF (150 ml) and methanol (50 ml) under stirring. After a few minutes, a solution 30% w/w in methanol of sodium methylate (0.28 mol) is added and ammonia is bubbled into the mixture for 8 hours. The reaction progress is followed by TLC until the complete conversion of the reactant. (Eluent: 48:16:32=toluene:methanol:THF and 4% of ammonia hydroxide concentrated).

When the reaction is completed, the solvent is removed using a rotary evaporator. The crude product is purified by crystallization from ethyl acetate and dried overnight at 50° C. under reduced pressure (yield 44%) obtaining an orange solid.

Anal. Calcd. For $C_9H_{10}N_4$: C, 62.05%, H, 5.79%, N: 32.16% Found: C %=61.52%, H %=5.59%, N %=32.89%; m.p.>300° C.

Intermediate Compound 11

In a 500 ml reaction flask, 124 g of the intermediate compound 3 (0.62 mol) are dissolved in THF (150 ml) and methanol (50 ml) under stirring. After a few minutes, a solution at 30% w/w in methanol of sodium methylate (0.25 mol) is added and ammonia is bubbled into the mixture for 12 hours. The reaction progress is followed by TLC until the complete conversion of the reactant (eluent: 48:16:32=toluene:methanol:THF and 4% of ammonia hydroxide concentrated). When the reaction is completed, the solvent is removed using a rotary evaporator. The crude product is purified by crystallization from ethyl acetate and dried overnight at 50° C. under reduced pressure, obtaining a yellow solid.

Anal. Calcd. For $C_{12}H_{16}N_4$: C %=66.64%, H %=7.46%, N %=25.90% Found: C %=65.97%, H %=7.42%, N %=26.61%; m.p.: 146-147° C.

A1) Preparation of Compound 101:
1,8(11),15(18),22(25)-Tetramethylamino manganese phthalocyanine

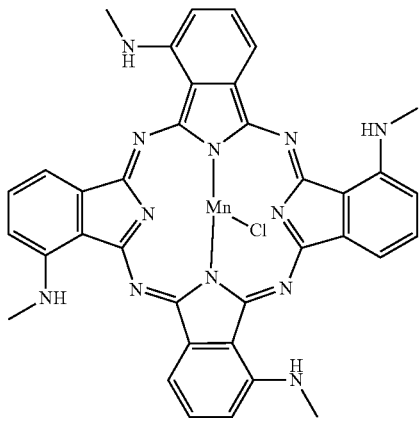

Compound 101

3-N-methyl-aminophthalonitrile intermediate compound 1 (16 g), magnesium chloride (3 g), 1,8-diazabicyclo[5.4.0]undec-7-ene (DBU, 3.8 g) are stirred together under nitrogen atmosphere for 16 h (T: 155° C.). Solvent used is n-hexanol (80 ml). After reaction time, the mixture is allowed to cool to room temperature and then filtered. Several washing cycles are performed (n-hexanol, methanol, water) with the crude material. The filtered product is dried under vacuum at 160° C. overnight and 16.4 g of a black powder are obtained (yield: 96%).

Anal. Calcd. For $C_{36}H_{28}ClMnN_{12}$: C, 60.13%; H, 3.92%; Cl, 4.93%; Mn, 7.64%; N, 23.37% Found: C, 59.80%; H, 3.96%; N, 21.62%; Mn (ICP):7.73%; Cl: 4.79%.

HPLC APCI-MS (negative polarization): m/z 718; mp>300° C.; UV-VIS (DMSO): $A_{max}$: 897 nm (ε: 82150).

A2) Preparation of Compound 102:
1,8(11),15(18),22(25)-Tetramethylamino vanadyl phthalocyanine

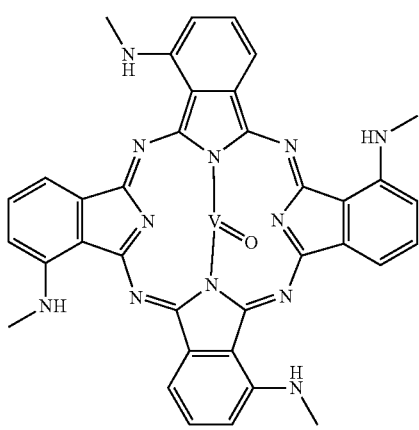

Compound 102

3-N-methyl-aminophthalonitrile (17 g), intermediate compound 1, vanadium chloride (4 g), 1,8-diazabicyclo[5.4.0]undec-7-ene (DBU, 12 g) are stirred together under nitrogen atmosphere for 16 h (T: 155° C.). Solvent used is n-hexanol (100 ml). After reaction time, the mixture is allowed to cool to room temperature and then filtered. Several washing cycles are performed (n-hexanol, methanol, water) with the crude material. The filtered product is dried under vacuum at 170° C. overnight and 6.0 g of a black powder are obtained (yield: 34%).

Anal. Calcd. For $C_{36}H_{28}N_{12}OV$: C, 62.16%; H, 4.06%; N, 24.16%; O: 2.30%; V: 7.32%. Found: C, 61.79%; H, 4.32%; N, 24.25%; V (ICP): 4.75%. HPLC APCI-MS (positive polarization): m/z (M$^+$+1) 696.3. mp>300° C. UV-VIS (CHCl$_3$): $A_{max}$: 824 nm (ε: 97881)

The following phthalocyanine compounds are prepared in analogy.

| Compound number | Intermediate number | Metal | UV-VIS (solv): $A_{max}$ | $ε_{\lambda max}$ |
|---|---|---|---|---|
| 103 | 2 | Mn | (CHCl$_3$) 876 nm | 58469 |
| 104 | 3 | Mn | (CHCl$_3$) 881 nm | 54202 |
| 105 | 4 | Mn | (CHCl$_3$) 882 nm | 60532 |
| 106 | 5 | Mn | (CHCl$_3$) 890 nm | 68446 |
| 107 | 6 | Mn | (CHCl$_3$) 826 nm | 51171 |
| 108 | 7 | Mn | (CHCl$_3$) 879 nm | 57255 |
| 109 | 1 | Cu | (DMSO) 782 nm | 4100 |
| 110 | 3 | Cu | (CHCl$_3$) 789 nm | 44731 |
| 111 | 1 | Al | (DMSO) 822 nm | 110354 |
| 112 | 1 | Co | (DMSO) 758 nm | 64052 |
| 113 | 1 | Sn | (CHCl$_3$) 865 nm | 32806 |
| 114 | 7 | Sn | (CHCl$_3$) 878 nm | 26265 |
| 115 | 1 | Zn | (CHCl$_3$) 772 nm | 19414 |
| 116 | 2 | Zn | (CHCl$_3$) 775 nm | 38776 |
| 117 | 3 | Zn | (CHCl$_3$) 778 nm | 91818 |
| 118 | 5 | Zn | (CHCl$_3$) 782 nm | 110932 |
| 119 | 6 | Zn | (CHCl$_3$) 741 nm | 68794 |
| 120 | 8 | Zn | (CHCl$_3$) 767 nm | 73040 |
| 121 | 1 | Ti=O | (CHCl$_3$) 834 nm | 43544 |
| 122 | 3 | Ti=O | (CHCl$_3$) 842 nm | 40691 |
| 123 | 4 | Ti=O | (CHCl$_3$) 814 nm | 76646 |

A3) Preparation of Compound 124:
1,8(11),15(18),22(25)-Tetramethylamino copper phthalocyanine

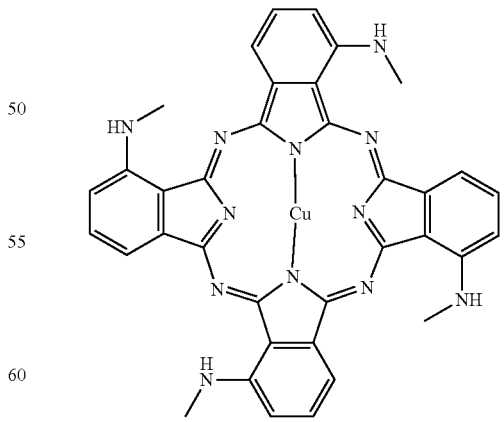

In a 250 ml reaction flask, 15 g of the intermediate compound 10 (0.086 mol) are dissolved in n-hexanol (150 ml) under stirring and after a few minutes, 3.4 g of CuCl$_2$ (0.02 mol) and 6.1 g of DBU (0.04 mol) are added. The reaction is then heated, refluxed for 16 h and filtered when cooled to room temperature. The solid is washed on the filter with 50 ml of methanol for two times. The solid product is finally dried overnight at 140° C. under reduced pressure, providing 13.8 g of a black powder.

Anal. Calcd. For $C_{36}H_{28}CuN_{12}$: C: 62.46%, H: 4.08%, N: 24.28%, Cu 9.18%. Found: C: 61.73%, H: 4.10%, N: 23.63%, Cu: 8.32%; HPLC APCI-MS (positive polarization) m/z=692.1; m.p.: >300° C.; UV-Vis (DMSO): $A_{max}$: 787 nm (ε: 3777)

A4) Preparation of Compound 125: 1,8(11),15(18),22(25)-Tetrabuthylamino copper phthalocyanine

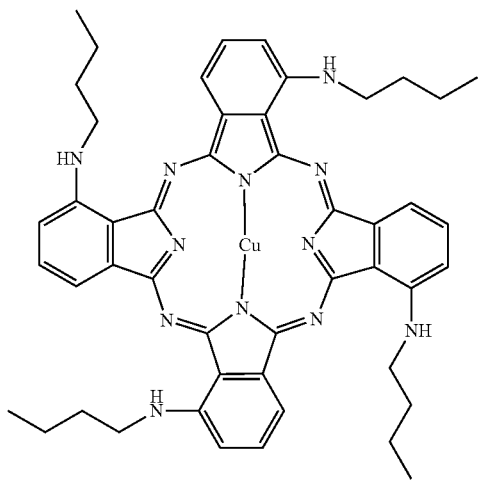

In a 250 ml reaction flask, 15.0 g of the intermediate compound 11 (0.07 mol) are dissolved in n-hexanol (100 ml) under stirring and after few minutes, 3.4 g of $CuCl_2$ (0.02 mol) and 3.2 g of DBU (0.02 mol) are added. The reaction is then heated at reflux for 16 h. When cooled to room temperature 50 ml of isopropanol are added, the crude is filtered and the solid obtained is washed twice with 20 ml of isopropanol. The solid product is finally dried overnight at 140° C. under reduced pressure, providing 8.9 g of a black powder.

Anal. Calcd. For $C_{48}H_{52}CuN_{12}$: C: 66.69%, H: 6.09%, N: 19.53%; Cu 7.38%. Found: C 63.84% H 6.01%, N 20.07%, Cu 6.88%. HPLC APCI-MS (positive polarization) m/z=860; m.p.: 250° C. (R) 280°-290° C.; UV-Vis ($CHCl_3$): $A_{max}$: 789 nm (ε: 44731)

B) APPLICATION EXAMPLES

B1) Examples of PC Injection Molding/PC Film Extrusion

Mixing and Compounding 3.0 kg of milled polycarbonate (Makrolon 3103) are dried in a vacuum oven at 120° C. for 8 hours. The powder is mixed with the additives listed in Table B1 for 3 minutes at 80° C. in a 5l Henschel Turbomixer and afterwards compounded on a Berstorff ZE 25×32D at 280° C. The polymer strand is granulated.

Sheet Extrusion

The pellets are used to produce a 100 μm thick cast film (plane) on a Collin CR-136/350 sheet extrusion line at a maximum temperature of 280° C.

Artificial Weathering

The samples are irradiated in a Weather-Ometer Ci65 from ATLAS in accordance with ASTM G 155/ASTM G 151, Xenon lamp with 2 borosilicate filters, 0.35 W/m2 at 340 nm, 63±3° C. black panel temperature, 102 min dry and light, 18 min water spray and light.

Evaluation

The ΔE values are measured in accordance with DIN 6174.

The UV-VIS-NIR Spectrum is recorded on a Shimadzu UV 3101 UV with ISR3100 integrating sphere: Parameter: Slit width 20, wavelength 250-1800 nm, Scan speed fast, Light Source change at 360 nm and Detector change at 830 nm.

The relative absorption is calculated by the absorption at the maximum divided by the initial absorption at the same wavelength.

Haze is measured on a Haze-gard plus from Byk Gardner in accordance with ASTM D-1003. The results are presented in Table B2.

PC Film sample, Thickness 100 μm: Initial Values

TABLE B1

| Structure | Conc. [%] | Initial Haze [%] | Absorption at max. | Max. [nm] | TINUVIN 360 [%] |
|---|---|---|---|---|---|
| 101 | 0.03 | 1.3 | 0.158 | 867 | 5 |
| 101 | 0.05 | 1.9 | 0.241 | 867 | 5 |
| 101 | 0.1 | 4.6 | 0.358 | 867 | 5 |
| 102 | 0.1 | 0.6 | 0.862 | 828 | 5 |
| 103 | 0.05 | 0.4 | 0.350 | 870 | 5 |
| 103 | 0.1 | 2.0 | 0.703 | 870 | 5 |
| 104 | 0.1 | 0.6 | 0.689 | 878 | 5 |
| 105 | 0.1 | 0 | 0.534 | 873 | 5 |
| 107 | 0.05 | 0.4 | 0.200 | 830 | 5 |
| 107 | 0.1 | 0.5 | 0.404 | 830 | 5 |
| 108 | 0.1 | 2.2 | 0.527 | 871 | 5 |

PC Film sample, Thickness 100 μm: Aged Samples

TABLE B2

| Structure | Conc. [%] | Haze after 500 hours WOM wet | ΔE after 500 hours WOM wet | Rel. Absorption after 500 hours WOM wet |
|---|---|---|---|---|
| 101 | 0.03 | 0 | 0.3 | 94% |
| 101 | 0.05 | 2 | 0.6 | 96% |
| 101 | 0.1 | 4.5 | 0.7 | 90% |
| 102 | 0.1 | 1.5 | 1.6 | 93% |
| 103 | 0.05 | 1.1 | 1.7 | 83% |
| 103 | 0.1 | 1.7 | 2.2 | 99% |
| 104 | 0.1 | 0.2 | 3.1 | 93% |
| 105 | 0.1 | 0.5 | 3.5 | 92% |
| 107 | 0.05 | 1.0 | 4.1 | 77% |
| 107 | 0.1 | 1.0 | 6.0 | 73% |
| 108 | 0.1 | 0.3 | 3.0 | 86% |

B2) Examples of MMA Polymerization

Sheet Preparation 70 g freshly distilled methylmethacrylate is polymerized with 0.1% lauroylperoxide, 0.15% TINUVIN P, 0.15% TINUVIN 770 and 0.01% Compound 102. after degassing. Firstly the mixture is prepolymerized at 60° C. in a twist-off glass for ca. 2 hours and then in a second step the syrup is polymerized between glass plates at 60° C. in a water bath followed 15 hours in oven followed by the final polymerization: 3 hours oven 120° C., resulting in a final thickness of ca. 1.8 mm.

Artificial Weathering

The samples were then irradiated in a Weather-Ometer Ci65 from ATLAS in accordance to ASTM G 155/ASTM G 151, Xenon lamp with 2 borosilicate filter, 0.35 W/m2 at 340 nm, 63±3° C. black panel temperature, dry cycle with relative humidity of ca. 50-60%)

Evaluation

The ΔE value was measured in accordance to DIN 6174

The UV-VIS-NIR Spectrum was recorded on a Shimadzu UV 3101 UV with ISR3100 integrating sphere: Parameter: Slit width 20, wavelength 250-1800 nm, Scan speed fast, Light Source change at 360 nm and Detector change at 830 nm.

TABLE B3

| Structure | Conc. [%] | Absorption at max. | Max. [nm] | TINUVIN 360 [%] TINUVIN 770 [%] | ΔE after 500 hours WOM wet | Rel. Absorption % after 500 hrs WOM wet |
|---|---|---|---|---|---|---|
| 102 | 0.01 | 0.141 | 800 | 0.15/0.15 | 6.3 | 89 |

B3) Examples of PET-G Film Extrusion

PET-G powder (Eastar 6763 from Eastman), 1% Tinuvin 1577, 0.1% of 1,8(11),15(18),22(25)-Tetramethylamino manganese phthalocyanine (compound 101) are turbo-mixed, dried at 70° C. for 12 hours, then compounded in a twin screw Collin Extruder. The obtained pellets are dried again and extruded in a Collin cast line to get a 300 micron PET-G film.

C) Evaluation of Heat Shielding

Samples containing solar controlling additives were evaluated using an internal equipment (see FIG. 1). This instrument compares the temperature build up of a black aluminum panel behind two plastic samples (A4 size), one sample containing the solar controlling additive the other being a reference without any additive. The two samples are mounted on the front side of two different chambers that are exposed to light of a 500 W halogen lamp with color temperature of 5000 K. To have the best accuracy two probes PT100 connected to a PC data logger are used.

The resulting heat shielding factor (HS) after 900 seconds, for a 300 micron PET-G film containing compound 101, as expressed by ΔT(° C)/900 sec. is 0.79.

The invention claimed is:

1. A transparent or translucent composition comprising
a) a compound of formula (I)

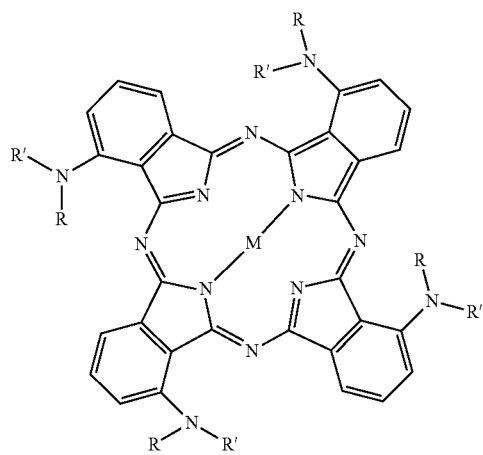

(I)

wherein

R is hydrogen, $C_1$-$C_{18}$alkyl, $C_3$-$C_{18}$alkyl interrupted by one or more O atoms, benzyl or cyclohexyl;

R' is hydrogen or $C_1$-$C_{18}$alkyl;

or R and R' together with the nitrogen atom to which they are bonded form a morpholine group; and M is Mn, Zn, V(O), Ti(O), Si, Al, Sn, Cu or Co;

which is dispersed in b) a thermoplastic or crosslinkable polymer;

wherein the composition is in the form of a sheet or film of a thickness of less than 10 mm and at least 80% translucent in each part of visible range of 400-800 nm;

wherein the sheet or film exhibits a full solar radiation of 340-1800 nm transmittance of less than 60%, a full visible light of 400-800 nm transmittance of more than 75% and a haze of less than 1% as measured according to ASTM D-1003, wherein the compound of formula (I) is present in an amount from 0.01 to 10% by weight, based on the weight of the thermoplastic or crosslinkable polymer.

2. The composition according to claim 1, wherein the thermoplastic or crosslinkable polymer comprises polycarbonate, a coating or coextruded layer on polycarbonate, polyesters, acrylics, halogenated polymers, polyolefins, aromatic homopolymers, copolymers derived from vinyl aromatic monomers, polyvinylacetales or blends, alloys or co-polymers thereof.

3. The composition according to claim 1, wherein the thermoplastic or crosslinkable polymer comprises polycarbonate, polymethylmethacrylate, polyethyleneterephthalate, polyvinylchloride, transparent ABS, polyvinylidene fluoride, styrene-acrylnitril copolymer, polypropylene, polyethylene or mixtures thereof.

4. The composition according to claim 1, containing as further component a conventional additive selected from antioxidants, flame retardants, clarifiers, UV absorbers and sterically hindered amines.

5. The composition according to claim 1, containing as further component tin oxide doped with antimony (ATO), tin oxide doped with indium (ITO), zinc oxide doped with aluminum (AZO), zinc oxide doped with indium (IZO), zinc oxide doped with gallium (GaZO), $LaB_6$, doped tungsten oxides ($YWO_x$), silver or gold nanoparticles, nanoprisms or nanorods or carbon nanotubes.

6. Architectural or automotive glazing in form of a monolithic sheet, a twin-wall sheet, a multi-wall sheet, a flat sheet or a corrugated sheet; or an agricultural film in form of a mono- or biaxially oriented film, a laminated film or a capstock film, comprising a composition according to claim 1.

* * * * *